(12) United States Patent
Yao et al.

(10) Patent No.: US 10,415,025 B2
(45) Date of Patent: Sep. 17, 2019

(54) FUNGUS-SOURCED HIGH-TEMPERATURE ACID B-GLUCOSIDASE AS WELL AS CODING GENE AND APPLICATION THEREOF

(71) Applicant: FEED RESEARCH INSTITUTE, CHINESE ACADEMY OF AGRICULTURAL SCIENCES, Beijing (CN)

(72) Inventors: Bin Yao, Beijing (CN); Pengjun Shi, Beijing (CN); Wei Xia, Beijing (CN); Huiying Luo, Beijing (CN); Huoqing Huang, Beijing (CN); Peilong Yang, Beijing (CN); Yaru Wang, Beijing (CN); Xiaoyun Su, Beijing (CN); Yingguo Bai, Beijing (CN); Xia Shi, Beijing (CN); Rui Ma, Beijing (CN)

(73) Assignee: FEED RESEARCH INSTITUTE, CHINESE ACADEMY OF AGRICU, Beijing (CN)

( * ) Notice: Subject to any disclaimer, the term of this patent is extended or adjusted under 35 U.S.C. 154(b) by 0 days.

(21) Appl. No.: 15/534,006

(22) PCT Filed: Dec. 8, 2014

(86) PCT No.: PCT/CN2014/093217
§ 371 (c)(1),
(2) Date: Jun. 8, 2017

(87) PCT Pub. No.: WO2016/090525
PCT Pub. Date: Jun. 16, 2016

(65) Prior Publication Data
US 2018/0073004 A1  Mar. 15, 2018

(51) Int. Cl.
| | | |
|---|---|---|
| C12N 9/42 | (2006.01) |
| C12N 15/00 | (2006.01) |
| C12N 1/20 | (2006.01) |
| C07H 21/04 | (2006.01) |
| C12P 21/06 | (2006.01) |
| C12P 21/04 | (2006.01) |
| C12N 1/14 | (2006.01) |
| A23K 20/189 | (2016.01) |
| A23L 33/10 | (2016.01) |
| A23L 29/00 | (2016.01) |
| A23K 10/14 | (2016.01) |

(52) U.S. Cl.
CPC .......... *C12N 9/2445* (2013.01); *A23K 20/189* (2016.05); *A23L 29/06* (2016.08); *A23L 33/10* (2016.08); *A23K 10/14* (2016.05); *A23V 2002/00* (2013.01)

(58) Field of Classification Search
None
See application file for complete search history.

(56) References Cited

PUBLICATIONS

Couger. KEY75643.1 GenBank Database. 2014.*
Studer. Residue mutations and their impact on protein structure and function: detecting beneficial and pathogenic changes. Residue mutations and their impact on protein structure and function: detecting beneficial and pathogenic changes. Biochem. J. (2013) 449, 581-594.*
Song. Comparison of three thermostable β-glucosidases for application in the hydrolysis of soybean isoflavone glycosides. J Agric Food Chem. Mar. 9, 2011;59(5):1954-61. doi: 10.1021/jf1046915. Epub Feb. 2, 2011.*

* cited by examiner

*Primary Examiner* — Yong D Pak
(74) *Attorney, Agent, or Firm* — Patshegen IP LLC; Moshie Pinchas

(57) ABSTRACT

Provided are a fungus-sourced high-temperature acid β-glucosidase as well as a coding gene, and an application thereof. The provide β-glucosidase has the optimal pH value of 4.5 and the optimal temperature of 75° C., and maintains over 90% enzyme activity in the optimal condition after being processed at 60° C. for 1 h. The re-engineering yeast strain GS115/bgl3A of the coding gene comprising the β-glucosidase has high fermentation level.

12 Claims, 2 Drawing Sheets
Specification includes a Sequence Listing.

FUNGUS-SOURCED HIGH-TEMPERATURE ACID Β-GLUCOSIDASE AS WELL AS CODING GENE AND APPLICATION THEREOF

FIELD OF THE INVENTION

The present invention relates to the field of genetic engineering, particularly to a fungi-derived high-temperature acid β-glucosidase, coding gene and application thereof.

BACKGROUND OF THE INVENTION

β-glucosidase (EC3.2.1.21) (β-D-glucoside glucohydrolase) can hydrolyze non-reducing β-D-glycosidic bond binding the end to release β-D-glucose and the corresponding ligands. β-glucosidase can catalyze the final reaction of decomposing cellulose to eliminate inhibition of cellobiose on exoglucanase and endoglucanase as the important component of cellulase system.

The β-glucosidase has important application value in medical treatment, food, and biomass energy conversion, and becomes more important since cellulose is the most widespread carbon source with energy crisis. It can fully hydrolyze straw fiber into glucose so as to be used to produce ethanol in fermentation. In the other hand, β-glucosidase can be applied to food industry by improving food's flavor and nutrition. Furthermore, β-glucosidase is widely used to hydrolyze soy isoflavones in feed industry and medicine.

β-glucosidase can be applied to industrial production of gentiooligsaccharide which can improve the flavor of the food.

The present invention provides a high-temperature acid β-glucosidase having high catalyzing activity and expression, so as to meet the requirement of industrial production, and biomass conversion.

SUMMARY OF THE INVENTION

One order of the present invention is to provide a fungi-derived high-temperature acid β-glucosidase.

Another order of the present invention is to provide a gene coding the above high-temperature acid β-glucosidase.

Another order of the present invention is to provide a recombinant vector comprising the above gene.

Another order of the present invention is to provide a recombinant cell comprising the above gene.

Another order of the present invention is to provide a method of preparing above high-temperature acid β-glucosidase.

Another order of the present invention is to provide an use of the above high-temperature acid β-glucosidase.

Thus, in one aspect, the present invention provided a novel high-temperature acid β-glucosidase, BGL3A which was separated from a thermophilic *Talaromyces emersonii* 12802, and a recombinant yeast highly expressing said β-glucosidase.

According to an embodiment of the present invention, was provided a high-temperature acid β-glucosidase which is selected from:
  (a) a polypeptide comprising the amino acid as shown in SEQ ID NO:1 or SEQ ID NO: 2;
  (b) a polypeptide with β-glucosidase activity which is derived from SEQ ID NO: 1 or SEQ ID NO. 2 by substitution, deletion and/or insertion of one or more amino acid residues.

```
SEQ ID NO: 1:
MLAEQIFLSVLAAAVTVQAYGFGGSGWDAAYGRAKAALNKLNQTEKVGIVT

GVKWMGGPCVGNTYKPSSIDYPSLCLQDSPLGVRFANPVTAFPAGINAGAT

WDRSLINARGAAMGAEAKGLGVNVQLGPVAGPLGKNPNSGRIWEGFSNDPY

LSGVAMEETIAGMQGSGVQACAKHYIGNEQEHNRETISSNIDDRTLHELYV

WPFMNAVKANVASVMCSYNEVNGSWSCENDALLNGLLKTELGFPGYIMSDW

NAQHTTVNSANSGLDMTMPGSDFNNPPGSIYWGPNLEAAVANGSVPQSRLD

DMVTRILASWYLVGQDEGYPPVAFSSWNGGKANVDVTGDHKSVVRAVARDS

IVLLKNDNNALPLRKPKSLAIIGQDATVNPAGPNACSDRGCDTGTLAMGWG

SGTAQFPYIVGPLDAIQSQAAADGTNITTSTTDDTTAAASAAASAGTAIVF

INSDSGEGYITVEGNAGDRNNLDPWHNGNELVQAVAAVNKNVIVVVHSVGP

VILEAILAQPNVKAIVWPGLPGQESGNALVDVLYGSTSPSGKLPYTIAKQF

SDYGTTWTTSLVDDFTEGLFIDYRHFDENNITPRYEFGYGLSYTTFKYSDL

DVNVQARPGAAEGPIVPGGVKELFDTVGTVTVTVQNSGKVAGAEVAQLYIG

LPDSAPSTPPKQLRGFQKLHLAPGQREGATFELTRRDISYWDVQQQKWVVP

SGTFKVYVGSSSRDIREQGSFRI
```

According to the embodiment of the present invention, said β-glucosidase comprises 737 amino acids, with a signal peptide of 19 amino acids in N-terminal, as set in forth in SEQ ID NO. 3.

According to the embodiment of the present invention, the mature β-glucosidase protein comprised the amino acid sequence set forth in SEQ ID NO: 2 having molecular weight of 76.3 kDa.

```
SEQ ID NO: 2
YGFGGSGWDAAYGRAKAALNKLNQTEKVGIVTGVKWMGGPCVGNTYKPSSI

DYPSLCLQDSPLGVRFANPVTAFPAGINAGATWDRSLINARGAAMGAEAKG

LGVNVQLGPVAGPLGKNPNSGRIWEGFSNDPYLSGVAMEETIAGMQGSGVQ

ACAKHYIGNEQEHNRETISSNIDDRTLHELYVWPFMNAVKANVASVMCSYN

EVNGSWSCENDALLNGLLKTELGFPGYIMSDWNAQHTTVNSANSGLDMTMP

GSDFNNPPGSIYWGPNLEAAVANGSVPQSRLDDMVTRILASWYLVGQDEGY

PPVAFSSWNGGKANVDVTGDHKSVVRAVARDSIVLLKNDNNALPLRKPKSL

AIIGQDATVNPAGPNACSDRGCDTGTLAMGWGSGTAQFPYIVGPLDAIQSQ

AAADGTNITTSTTDDTTAAASAAASAGTAIVFINSDSGEGYITVEGNAGDR

NNLDPWHNGNELVQAVAAVNKNVIVVVHSVGPVILEAILAQPNVKAIVWPG

LPGQESGNALVDVLYGSTSPSGKLPYTIAKQFSDYGTTWTTSLVDDFTEGL

FIDYRHFDENNITPRYEFGYGLSYTTFKYSDLDVNVQARPGAAEGPIVPGG

VKELIDTVGTVTVTVQNSGKVAGAEVAQLYIGLPDSAPSTPPKQLRGFQKL

HLAPGQREGATFELTRRDISYWDVQQQKWVVPSGTFKVYVGSSSRDIREQG

SFRI
```

The β-glucosidase of the present invention has high temperature tolerance, high acid tolerance, and high catalytic efficiency. The β-glucosidase of the present invention from *Talaromyces emersonii* 12802 has the optimal pH value of 4.5 and the optimal temperature of 75° C., is thermostable at 37° C., and maintains over 90% of activity in the optimal condition after being processed at 60° C. for 1 h.

Yet another aspect of the invention is a gene coding the above high-temperature acid β-glucosidase, with the following characteristics:
(a) coding a polypeptide comprising the amino acid as shown in SEQ ID NO. 1 or SEQ ID NO. 2;
(b) coding a polypeptide with β-glucosidase activity which is derived from SEQ ID NO: 1 or SEQ ID NO. 2 by substitution, deletion and/or insertion of one or more amino acid residues.

Preferably, the gene coding the above high-temperature acid β-glucosidase according to the embodiment of the present invention is selected from
(a) DNA comprising a nucleotide sequence set in forth in SEQ ID NO.4 or SEQ ID NO.5; or
(b) DNA hybridizing under stringent conditions, to a nucleotide sequence set in forth in SEQ ID NO.4 or SEQ ID NO.5, and coding polypeptide with glucosidase activity.

Preferably, said gene has a nucleotide sequence set in forth in SEQ ID NO.4.

agcgccgcactccagtattccggtgatttccagcgacattgatgcggggaa
ggaatcaaggggacatcatccctggaattcctataagatggccgtcaccca
cgcatgaaaaataaaanatgctccttttgatntgcgactcgagtacccaca
gcgacagcgacgatcaccatgcttgctgagcaaatcttcctgagtgttctg
gcagcagccgtcactgtccaggcctatggcttcggcggctctggctgggac
gccgcttatggcagagcaaaggctgcgctgaacaagntcaaccagaccgag
aaggttggtatcgtcaccggtgtcaagtggatgggcggcccttgtgttggc
aacacctacaagcccagttcgattgantaccttctctgtgtttgcaagac
tctcctctcggggtgcgttttgccaaccctgtgactgccttcccggntggt
atcaacgccggcgccacatgggatagatctctcatcaacgcccgtggtgcg
gccatgggcgctgaggccaagggcctcggtgtgaacgtccagcttggcccc
gtcgctggtcctctcggcaagaatcccaatagtggcagaatctgggaaggg
actcgaatgatccctatctcagcggtgagcgatggaggaaaccatcgccgg
aatgcaaggatctggtgtgcaggcctgcgccaaggtacgtggatctcgact
tgcaacatgtacgatctgagagggctgacacgatacctgaatctatagcac
tatattggtaacgagcaagagcacaaccgtgaaaccatcagctccaacatc
gatgaccgcactctgcacgagctctacgtctggccgttcatgaacgccgtc
aaggccaacgtcgcctccgtcatgtgctcgtacaacaaggtcaatggttcc
tggtcctgtgagaatgatgctcactcaacggtctgagaagactgagctcgg
attccccggatacatcatgagcgattggaacgcgcagcacaccacggtcaa
cagcgccaactcggtctcgatatgaccatgcctggcagtgacttcaacaa
ccctcctggcagcatctgctggggccaacctcgaagccgccgtcgccaa
tggctccgaccgcagtcccgtaggacgacatggtcactcgtatccagcgtc
aggcacttggaggccaggatgagggctacccaccggtcgccttcagctcct
ggaatgcggcaaggccaatgttgacgtgacgggcgatcacaagagcgtcg
tcagagctgtggctcgtgactctaccgttcactgaagaacgacaataacgc tagcctctgcgcaagcccaagagcctcgcgatcatcggccaggatgcaacc
gtcaaccctgccgggcccaacgcttgctctgatcgcggctgcgacactggt
actctcgccatgggagggcagtggtaccgctcagacccagtgagtcgtcc
cattgcaacttccacaggagcgaccggtgactaacaagcacctagtacatc
gtcggccctctcgatgctatccagtctcaggctgccgctgatggcactaac
atcaccaccagcgcgaccgatgataccaccgcggcagatctgcagccgcct
ccgccggaaccgccatcgtcttcatcaactccgactctggtgaagggtaag
cccgggcgtcaagatcctcgtacagatgggcccgcatcgctaacattctac
agttacatcaccgtcgagggcaacgctggtgaccgcaacaacctcgacccc
tggcacaacggcaacgagctcgtccaggccgttgcggctgcgaacaagaat
gtcattgtcgtcgtccacagcgtcggtcccgtgatcaggagactatccttg
cacagcccaacgtcaaggccattgtgtggcccggtctccctggacaagaga
gcggcaatgccctggtcgatgactgtacggctccacctcccccagcggcaa
gagccctataccattgccaagcagttcagcgactatggctccacctggacg
acctccctggtcgatgacttcaccgagggtctgacattgactaccgccact
agacgagaacaacattactcccagatacgagttcggatacggcagtgttag
tacttcatctctctctcgtagatccatgctgtcatgcaacgacacaaactg
acatgataatagcttacaccaccacaaatactccgacctggacgtcaacgt
ccaggcccgccccggcgcagccgaaggcccatcgtcccggcggcgtcaa
ggaactatcgacaccgtcggcaccgtcaccgtcaccgtccagaacagcggc
aaggagccggcgcggaagttgcccagctgtacatcggccttcccgactctg
ccccgtcgaccctcccaagcagctcagaggattccagaagttgcacctcg
cgcccggccagagagagggcgccactacgaactcacccgccgagacatcag
ctactgggacgttcagcagcagaagtgggttgacctagcggtacgttcaag
gtctatgaggaagctcgagcagggacattagggagcagggatcttgagtac
gagcacatgacggaggcgacgttgaccgtggtgtgctgcgcgaccaatc According to an embodiment of the present invention, the gene coding β-glucosidase isolated by PCR method, was 2214 bp in length, comprising a nucleotide sequence set in forth in SEQ ID NO.6 coding a signal peptide.

atgcttgctgagcaaatcttcctgagtgttctggcagcagccgtcactgtccag-gcc (SEQ ID NO.6).

A gene coding a mature β-glucosidase had a nucleotide sequence set in forth in SEQ ID NO.5.

SEQ ID NO. 5
tatggcttcggcggctctggctgggacgccgcttatggcagagcaaaggct
gcgctgaacaagctcaaccagaccgagaaggaggtatcgtcaccggtgtca
agtggatgggcggcccagtgaggcaacacctacaagcccagttcgattgac
taccactctgtgatgcaagactctcctctcggggtgcgattgccaaccct
gtgactgccacccggctggtatcaacgccggcgccacatgggatagatctc
tcatcaacgcccgtggtgcggccatgggcgctgaggccaagggcctcggtg
tgaacgtccagcaggcccgtcgctggtcctctcggcaagaatcccaatag
tggcagaatctgggaagggactcgaatgatccctatctcagcggtgagcga -continued

```
tggaggaaaccatcgccggaatgcaaggatctggtgtgcaggcctgcgcca agcactatattggtaacgagcaagagcacaaccgtgaaaccatcagctcca acatcgatgaccgcactctgcacgagctctacgtctggccgttcatgaacg ccgtcaaggccaacgtcgcctccgtcatgtgctcgtacaacgaggtcaatg gttcctggtcctgtgagaatgatgctcttctcaacggtctgttgaagactg agctcggattccccggatacatcatgagcgattggaacgcgcagcacacca cggtcaacagcgccaactcgggtctcgatatgaccatgcctggcagtgact tcaacaaccctcctggcagcatctactgggggcccaacctcgaagccgccg tcgccaatggctccgaccgcagtcccgtttggacgacatggtcactcgtat ccttgcgtcttggtacttggttggccaggatgagggctacccaccggtcgc cttcagctcctggaatggcggcaaggccaatgagacgtgacgggcgatcac aagagcgtcgtcagagctgtggctcgtgactctatcgttcttctgaagaac gacaataacgctttgcctctgcgcaagcccaagagcctcgcgatcatcggc caggatgcaactgtcaaccctgccgggcccaacgcttgctctgatcgcggc tgcgacaccggtactctcgccatgggaggggcagtggtaccgctcagaccc atacatcgtcggccctctcgatgctatccagtctcaggctgccgctgatgg cactaacatcaccaccagcacgaccgatgataccaccgcggcagatctgca gccgcctccgccggaaccgccatcgtatcatcaactccgactctggtgaag gttacatcaccgtcgagggcaacgctggtgaccgcaacaacctcgaccccct ggcacaacggcaacgagctcgtccaggccgttgcggctgtgaacaagaatg tcattgtcgagtccacagcgtcggtcccgtgatcaggaggctatccttgca cagcccaacgtcaaggccattgtgtggcccggtctccctggacaagagagc ggcaatgccctggtcgatgactgtacggctccacctcccccagcggcaaga gccctataccattgccaagcagttcagcgactatggcaccacctggacgac ctccctggtcgatgacttcaccgagggtctgacattgactaccgccaattg acgagaacaacattactcccagatacgagttcggatacggatgtcttacac caccacaaatactccgacctggacgtcaacgtccaggcccgccccggcgca gccgaaggcccatcgtccccggcggcgtcaaggaactatcgacaccgtcg gcaccgtcaccgtcaccgtccagaacagcggcaaggagccggcgcggaaga gcccagctgtacatcggccacccgactctgccccgtcgaccctcccaagc agctcagaggattccagaagagcacctcgcgcccggccagagagagggcgc cactacgaactcacccgccgagacatcagctactgggacgttcagcagcag aagtgggttgttcctagcggtacgttcaaggtctatgttggaagctcgagc agggacattagggagcagggatctttccgtatttga
```

The molecular mass of the mature protein is 76.3 kDa. Homology searches in GenBank were done using the BLAST server. As a result, the amino acid sequence (SEQ ID NO: 1) showed a homology (83%) with the known β-glucosidase from *Neosartorya fischeri* NRRL 181, and had a homology (82%) with β-glucosidase from *Aspergillus fumigatus* Af293. Therefore, it was conformed that the ORF from *Talaromyces emersonii* 12802 coded a novel β-glucosidase. The amino acid sequence of ORF from *Talaromyces emersonii* 12802 was named BGL3A like other name of β-glucosidase.

The present invention also provides to an isolated protein comprising the amino acid sequence depicted in SEQ ID NO: 1 or SEQ ID NO: 2. In another embodiment, the present invention relates to a derivate of said protein, which is obtainable from SEQ ID NO: 1 or SEQ ID NO: 2 by substitution, deletion and/or insertion of one or more (e.g., one or several, or a value selected from 1-10, e.g., 1, 2, 3, 4, 5, 6, 7, 8, 9 or 10, or ranges intermediated to the above-recited values) amino acid residues, and maintains the β-glucosidase activity. For example, a common strategy is conservative amino acid substitutions that is to say, the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, replacement with another amino acid residue from the same side chain of one or more amino acid residue would not substantially change the enzyme activity of said β-glucosidase. Furthermore, it is well known in the art that during the cloning of genes, usually enzyme recognition sites are designed, which would result in one or several non-relating amino acid residues on the ends of target protein without affecting the activity thereof. In addition, in order to construct a fusion protein, to enhance expression of recombinant protein, to obtain an recombinant protein automatically secreted outside the host cell, or to aid in the purification of the recombinant protein, suitable peptide linker, signal peptide, leader peptide, terminal extensions, glutathione S-transferase (GST), maltose E binding protein, protein A, tags such as 6His or Flag, or proteolytic cleavage site for Factor Xa, thrombin or enterokinase are usually introduced into the N- or C-terminus of the recombinant protein or within other suitable regions in the proteins.

In another embodiment, the protein with β-glucosidase activity according to the present invention can comprise an amino acid sequence which is encoded by a nucleotide sequence which hybridizes, e.g., hybridizes under stringent conditions, to a nucleotide sequence of SEQ ID NO: 4 or SEQ ID NO:5 as set forth in the Sequence Listing. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to one of ordinary skill in the art and can be found in *Current Protocols in Molecular Biology*, John Wiley & Sons, N.Y. (1989), 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50-65° C. A person skilled in the art understands that high stringent condition could be realized by raising the hybridization temperature up to 50° C., 55° C., 60° C. or 65° C.

Besides, it will be appreciated by one of ordinary skill in the art that genetic polymorphism due to natural variation may exist among individuals within a population. Such natural variations can typically result in 1-5% variance in the nucleotide sequence of the (3-glucosidase gene. Any and all such nucleotide variations and resulting amino acid polymorphisms in β-glucosidase that are the result of natural variation and that do not alter the functional activity of β-glucosidase proteins are intended to be within the scope of the invention. Therefore, the present invention also encompasses a polypeptide with β-glucosidase activity encoded by such an allele or natural variant of the polynucleotide as shown in SEQ ID NO: 4 or SEQ ID NO.5.

In a preferred embodiment, a β-glucosidase protein is such a active protein that is at least about 60%, 61%, 62%, 63%, 64%, 65%, 66%, 67%, 68%, 69%, or at least about 70%, 71%, 72%, 73%, 74%, 75%, 76%, 77%, 78%, 79%, or at least about 80%, 81%, 82%, 83%, 84%, 85%, 86%, 87%, 88%, 89%, or at least about 90%, 91%, 92%, 93%, 94%, 95%, 96%, 97%, 98%, more preferably at least about 98.1%, 98.2%, 98.3%, 98.4%, 98.5%, 98.6%, 98.7%, 98.8%, 98.9%, and even more preferably at least about 99%, 99.1%, 99.2%, 99.3%, 99.4%, 99.5%, 99.6%, 99.7%, 99.8%, 99.9% or more homologous to the entire amino acid sequence as shown in SEQ ID NO: 1 or SEQ ID NO: 2 of the present invention. Ranges and identity values intermediated to the above-recited values (e.g., 60-90% homologous or 98.1-99.9% identical) are also intended to be included in the present invention.

On the other hand, the present invention provides a novel β-glucosidase gene of SEQ ID NO: 4 or SEQ ID NO:5. The invention further encompasses nucleic acid molecules that differ from one of the nucleotide sequences depicted in SEQ ID NO: 4 or SEQ ID NO: 5 of the invention due to degeneracy of the genetic code and thus encode the same β-glucosidase protein. In another embodiment, an isolated nucleic acid molecule of the invention is a nucleotide sequence which hybridizes, e.g., hybridizes under stringent conditions, to a nucleotide sequence of SEQ ID NO: 4 or SEQ ID NO:5, with the allele or natural variant thereof is preferred. In another embodiment, an isolated nucleic acid molecule of the invention has a nucleotide sequence encoding a protein having an amino acid sequence shown in the SEQ ID NO: 1 or SEQ ID NO:2. In a still further embodiment, the nucleic acid molecule of the invention encodes a full length β-glucosidase protein which is substantially homologous to an amino acid sequence of SEQ ID NO: 4 or SEQ ID NO: 5, for example, a protein that derived from SEQ ID NO: 1 or SEQ ID NO:2 by substitution, deletion and/or insertion of one or more (e.g., one or several, or a value selected from 1-10) amino acid residues, or one that is at least 99% homologous to the amino acid sequence of SEQ ID NO: 1 or SEQ ID NO:2. Such a nucleic acid molecule is preferably at least about 60%, 61%, 62%, 63%, 64%, 65%, 66%, 67%, 68%, 69%, or at least about 70%, 71%, 72%, 73%, 74%, 75%, 76%, 77%, 78%, 79%, or at least about 80%, 81%, 82%, 83%, 84%, 85%, 86%, 87%, 88%, 89%, more preferably at least about 90%, 91%, 92%, 93%, 94%, 95%, 96%, 97%, 97.7%, 97.8%, 97.9%, or at least about 98%, 98.1%, 98.2%, 98.3%, 98.4%, 98.5%, 98.6%, 98.7%, 98.8%, 98.9%, and even more preferably at least about 99%, 99.1%, 99.2%, 99.3%, 99.4%, 99.5%, 99.6%, 99.7%, 99.8%, 99.9% or more homologous to a nucleotide sequence of SEQ ID NO: 4 or SEQ ID NO:5. Ranges and identity values intermediate to the above-recited values (e.g., 76-97% homologous or 97.8-99.9% identical) are also intended to be included in the present invention.

In yet another embodiment, the present invention relates to a recombinant vector comprising said nucleic acid coding said β-glucosidase, a recombinant host cell (such as *Pichia Pastoris*, yeast, and *E. coli.*) having been introduced said vector or said nucleic acid molecule, as well as a method for expressing the enzyme in a host cell. In a preferred embodiment, said β-glucosidase gene was controlled by promoter AOX1 by being inserted between sites of EcoRI and NotI in plasmid pPIC9, so as to obtain the recombinant expression vector pPIC9-bgl3A.

In a preferred embodiment, said recombinant host cell was strain GS115/bgl3A.

The present invention relates to a method of producing the said β-glucosidase, including the steps:
 (a) cultivating the host cells to provide the supernatant containing the said β-glucosidase; and
 (b) recovering the said β-glucosidase.

The recombinant expression vectors of the invention can be designed for expression of β-glucosidase proteins in prokaryotic or eukaryotic cells. For example, β-glucosidase gene can be expressed in bacterial cells such as *E. coli*, yeast such as *Pichia* or *Aspergillus*, insect cells (e.g., Sf9 cell or silkworm cell, using baculovirus expression vectors), or plant cell (such as *Arabidopsis*, tobacco, corn, and so on, mediated by *Agrobacterium tumefaciens*). Thus, the invention pertains to host cells into which a recombinant expression vector of the invention has been introduced, with *Pichia* preferred. *Pichia pastoris* is a methylotrophic yeast, capable of metabolizing methanol as its sole carbon source. This system is well-known for its ability to express high levels of heterologous proteins. As an effective expression system, many of β-glucosidase gene have successfully expressed in *P. pastoris*. The novel β-glucosidase gene also expressed in *P. pastoris* and had high levels of expression. The extracellular β-glucosidase activity is 33 U/ml for the induced expression in a large flask, and more than 3400 U/ml for the induced expression in tank, respectively. So it will be very easy to mass-produce the β-glucosidase by fermentation, and the cost will be lower than ever.

Vector DNA can be introduced into prokaryotic or eukaryotic cells via conventional transformation or transfection techniques. As used herein, the terms "transformation" and "transfection", "conjugation" and "transduction" are intended to refer to a variety of art-recognized techniques for introducing foreign nucleic acid (e.g., linear DNA or RNA (e.g., a linearized vector or a gene construct alone without a vector) or nucleic acid in the form of a vector (e.g., a plasmid, phage, phasmid, phagemid, transposon or other DNA) into a host cell, including calcium phosphate or calcium chloride co-precipitation, DEAE-dextran-mediated transfection, lipofection, natural competence, chemical-mediated transfer, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

A host cell of the invention, such as a prokaryotic or eukaryotic host cell in culture, can be used to produce (i.e., express) a β-glucosidase protein. Accordingly, the invention further provides methods for producing β-glucosidase proteins using the host cells of the invention. In one embodiment, the method comprises culturing the host cell of invention (into which a recombinant expression vector encoding a β-glucosidase protein has been introduced, or into which genome has been introduced a gene encoding a wild-type or altered β-glucosidase protein) in a suitable medium until β-glucosidase protein is produced. In another embodiment, the method further comprises isolating β-glucosidase proteins from the medium or the host cell.

Yet another aspect of the invention is the β-glucosidase expressed in *Pichia pastrois*. In order to ascertain the assay of the β-glucosidase, the β-glucosidase was purified by simple approach, such as ammonium sulfate precipitation, dialysis, ultrafiltration and chromatography. After the simple purification, the purity of the β-glucosidase was enough to study the enzyme properties.

Yet another aspect of the invention is the application of said β-glucosidase to the food industry, the feed industry, and the biomass energy.

With the aim to solve the problem of the low activity of the microorganism producing β-glucosidase existing in the art, we had isolated a novel β-glucosidase from *Talaromyces emersonii* 12802. We had also identified the nucleotide sequence, which codes the protein having β-glucosidase. The β-glucosidase had several advantages: high specific activity, favourable pH-optimum, high stability at higher temperatures, resistance against proteases, easily produce by fermentation. The β-glucosidase was an acidic enzyme showing a high enzyme activity at 60° C.-75° C. and the optimal activity was observed at 75° C. The enzyme activity was very stable between pH 1.0 and pH 10.0, the optimal pH was 4.5. And the enzyme had a high stability at higher temperatures, when the enzyme was left at 60° C. for 1 hour, 90% of the activity was remained.

BRIEF DESCRIPTIONS OF THE DRAWINGS

EXAMPLES

Figure 1:
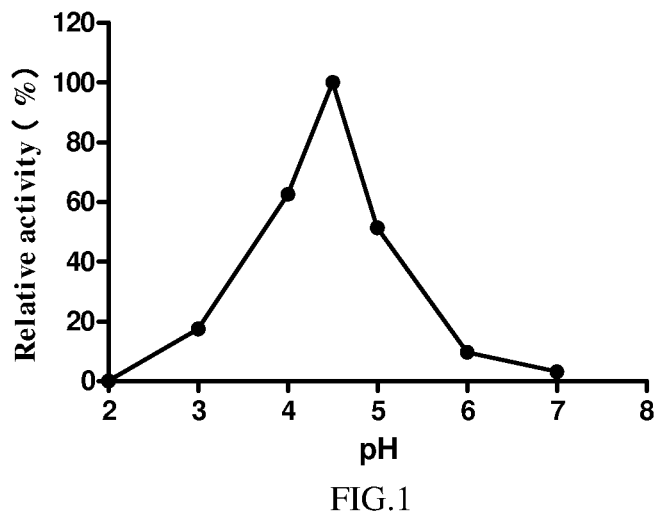
FIG. 1 shows optimum pH values for novel β-glucosidase.

The present invention is further illustrated with reference to the following Examples and the appended drawings, which should by no means be construed as limitations of the present invention.

Test Materials and Reagents

1. Strains and vectors: *Talaromyces emersonii* 12802; *Pichia pastoris* strain GS115 (Invitrogen); and vetor pPIC9 (Invitrogen, San Diego, Calif.).
2. Enzymes and other biochemical reagents: restriction endonucleases(TaKaRa); ligase (Invitrogen); and birch xylan(Sigma)
3. Medium:
   (1) taking potato dextrose medium as *Talaromyces emersonii* 12802 Medium, including 1000 mL of potato juice, 10 g of dextrose, and 25 g of arga, natural pH.
   (2) *E. coli*. LB medium: 1% of peptone, 0.5% of yeast extract, and 1% of NaCl, natural pH.
   (3) BMGY medium: 1% of yeast extract; 2% of peptone; 1.34% of YNB, 0.00004% of Biotin; and 1% of glycerol(V/V).
   (4) BMMY medium: 1% of yeast extract; 2% of peptone; 1.34% of YNB, 0.00004% of Biotin; and 0.5% of methanol (V/V).

Suitable biology laboratory methods not particularly mentioned in the examples as below can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other kit laboratory manuals.

Example 1 Cloning β-Glucosidase Gene from *Talaromyces emersonii* 12802

Genomic DNA is isolated from *Talaromyces emersonii* 12802 by adding 2 mL of extract buffer mycelium, and grinding for 5 min, followed by decomposing for 120 min in a water bath at 65° C., and mixing well every 20 min, then centrifugating for 10 min at 13000 rpm at 4° C. The supernatant was extracted in phenol/chloroform to remove the impurities, followed by adding isopropanol in equal volume, settling for 30 min at −20° C., centrifugating for 10 min at 13000 rpm at 4° C. to remove supernatant, washing the precipitate with 70% ethanol twice followed by drying, dissolving in TE solution and storing at −20° C.

It was possible to design a pair of degenerate primers to amplify part fragment of the (3-glucosidase gene based on the conserved fragment of the family 3 of β-glucosidase from the *Talaromyces emersonii* 12802 DNA by PCR.

P1:
(SEQ ID. NO. 7)
5'-GGCCGCAAYTGGGARGGNTT-3';

P2:
(SEQ ID. NO. 8)
5'-GTCACCAGGCATNGHCATRTC-3'.

PCR amplification was performed by optimizing PCR parameters as follows: degenerating at 94° C. for 5 minutes, followed by 30 cycles at: degenerating at 94° C. for 30 seconds/annealing temperature at 45° C. for 30 seconds/extending at 72° C. for 1 minute, and a final extension of 10 minutes at 72° C. PCR product comprising 475 bp was obtained and linked to vector pEASY-T3 for sequencing.

Based on the known 475 bp fragment, the nested insertion-specific primers for TAIL PCR were designed, and named respectively as shown in table 1, wherein primer sp2 located in the downstream of primer sp1, primer sp3 located in the downstream of primer sp2, the arbitrary distance between two primer, 22~30 nt in length, and the annealing temperature at 60~65° C.

TABLE 1

Specific primers for TAIL PCR

| Primer | Sequence (5'---3')<br>SEQ ID NO. | Length (bp) |
|---|---|---|
| dsp1 | CGAGGACGGAACCTACCGCGAGAGC/9 | 25 |
| dsp2 | CGAGGAGTACATCAAGCTTGCCTTCG/10 | 26 |
| dsp3 | CAAGGTCGACCCTAAGGCCAAGC/11 | 23 |
| usp1 | GTAGAGCTTGGCCTTAGGGTCGAC/12 | 24 |
| usp2 | GCGGCGGTCTCGAAGGCAAGCTTG/13 | 24 |
| usp3 | GGTAGGTTCCGTCCTCGTTCAGCG/14 | 24 |

Two flanking sequences were obtained by Reverse TAIL-PCR, sequenced, and assembled into β-glucosidase gene with 2682 bp in full length including five introns, coding 773 amino acids and one termination codon. Said β-glucosidase gene comprised a mature gene of 2214 bp and a fragment coding signal peptide of 19 amino acids in N-terminal.

Example 2 Producing Recombinant β-Glucosidase

The coding region of mature protein was amplified. The amplification products were visualized by electrophoresis on agarose gel, and band of expected size was excised and DNA was extracted with Kit. The DNA purified was inserted into pPIC9 (Invitrogen, San Diego, Calif.) at the EcoRI and NotI sites, as described by the manufacturer instruction to obtain DNA construct pPIC-bgl3A. The construct was transformed into *Pichia pastoris* strain GS115 to obtain the recombinant cell GS115/bgl3A.

The transformed *Pichia pastoris* strain GS115 (Invitrogen) were incubated in 400 mL of BMGY for 48 h at 30° C. and 250 rpm, and then the cells were spun down and suspended in 200 mL of BMMY to induce the β-glucosidase gene expression. 72 hours after induction, the supernatant was recovered by spinning to test the activity of the β-glucosidase. The expression amount of β-glucosidase was 33 U/mL. And, the recombinant β-glucosidase was expressed in *Pichia pastoris* strain GS115 as showed by SDS-PAGE.

The expression vector comprising the full-length β-glucosidase gene was constructed and transformed to *Pichia pastoris* strain GS115 by the same method as above, and the recombinant β-glucosidase was also tested.

Example 3 Measuring Activity of the Recombinant β-Glucosidase

The amount of pNP produced by hydrolyzing substrate pNPG with enzyme in 405 nm. 125 μl of substrate solution of pNPG in 2 mM mixed with 125 μl buffer was added to 250 μl of diluted enzyme solution, which was reacted at 60° C. for 10 minutes. Then, 1.5 mL of $Na_2CO_3$ in 1M was added to stop the reaction. OD 405 was measured.

1 unit of β-glucosidase activity was determined to be the enzyme amount releasing 1 μmol of pNP by decomposing substrate, pNPG, for 1 minute.

Example 4 Measuring the Properties of the Recombinant β-Glucosidase Obtained in Example 2

1. Optimum pH Values and pH Stability

Figure 2:
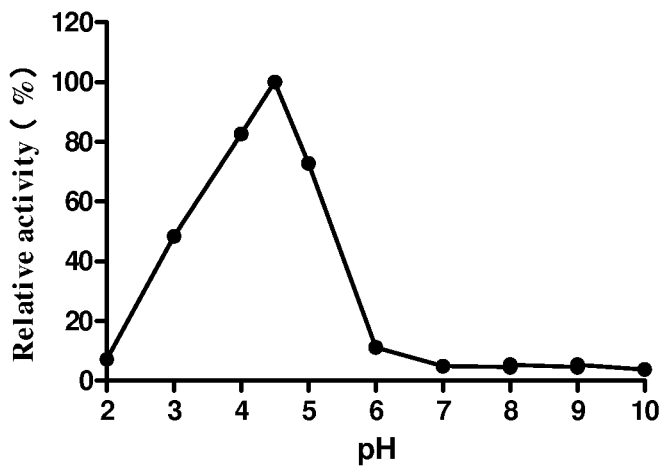
FIG. 2 shows pH stabilities for novel β-glucosidase.

The β-glucosidase purified in example 2 was reacted in the different pH to determine optimum pH. The activity of β-glucosidase was measured with xylan in 0.1 mol/L citric acid-sodium dimetallic phosphate buffer with different pH at 50° C. As is shown in FIG. 1, the activity of β-glucosidase varied with pH. The highest activity was observed at pH 4.5. Part of the activity was still maintained at pH 3.0. FIG. 2 shows the enzyme activity was very stable, when the β-glucosidase was maintained at 37° C. at different pH for 60 min followed by measuring the activity in buffer with pH 4.5 at 75° C.

2. Optimum Temperature and Heat Stability

Figure 3:
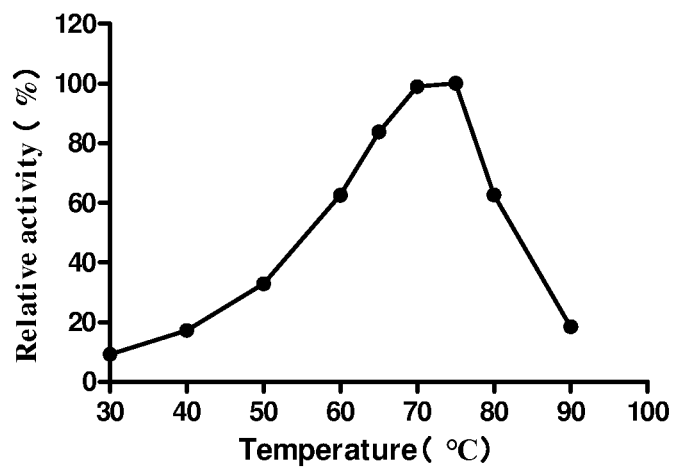
FIG. 3 shows optimum temperature values for novel β-glucosidase.
Figure 4:
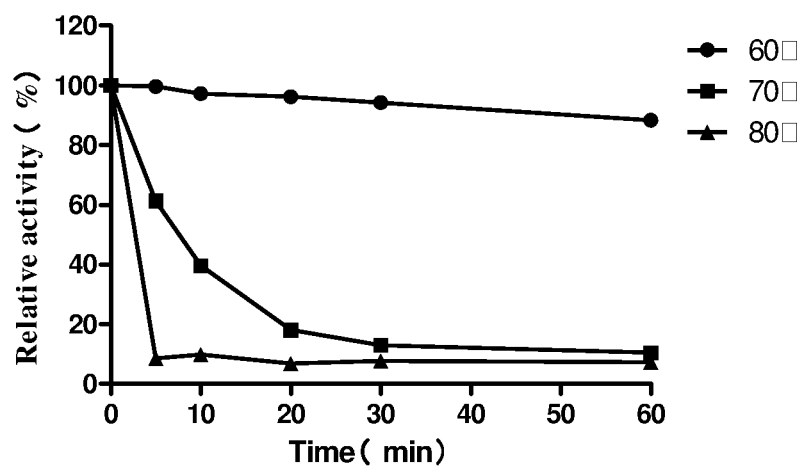
FIG. 4 shows heat stability for novel β-glucosidase.

The β-glucosidase was reacted in the different temperatures to determine optimum temperature. The activity of β-glucosidase was measured with xylan in citric acid-sodium dimetallic phosphate buffer (pH 6.0) at different temperatures. As shown in FIG. 3, the activity of β-glucosidase varied with temperatures. The highest activity was observed at 75° C. FIG. 4 showed the enzyme activity was thermal-stable, more than 90% of the enzyme activity was still maintained when the enzyme was maintained at 60° C. for 1 h.

3. Measuring Enzyme Kinetics of β-Glucosidase

Testing the activity of β-glucosidase at 75° C. with the different concentration of substrate, pNPG, in citric acid-sodium dimetallic phosphate buffer (pH4.5), and calculating $K_m$ as 0.18 mM, and $V_{max}$ as 1308.73 μmol/min·mg.

4. Effect of Metal Ions and Inhibitors on Activity of β-Glucosidase

The effect of metal ions on β-glucosidase activity was investigated at the pH optimum (pH 4.5) and 75° C. in a final concentration of 5 mmol/L. The result showed that, among various metal ions, the enzyme activity of β-glucosidase was weakly inhibited by many metal ions. As for inhibitors, the enzyme activity was strongly tolerant to SDS, and 78% of the enzyme activity was remained in SDS concentration of 5 mmol/L. However, the enzyme activity was inhibited by $Ag^+$ and $Cu^{2+}$.

5. Determination of Specific Activity

As showed in table 2, β-glucosidase BGL3A was specific, specifically hydrolizing aglycone of non-reducing end, almost didn't hydrolyze fiber polysaccharides.

TABLE 2

Specific activity of β-glucosidase BGL3A

| Substrate | Specific activity (U/mg) |
| --- | --- |
| p-Nitrophenyl β-d-glucoside | 826.9 ± 0.12 |
| p-Nitrophenyl β-d-cellobioside | 76.57 ± 0.03 |
| p-nitrophenyl β-d-xylopyranoside | 65.23 ± 0.11 |
| p-nitrophenyl β-d-galactoside | 103.71 ± 0.07 |
| p-nitrophenyl α-l-arabinofuranoside | 72.94 ± 0.18 |
| p-nitrophenyl | 76.76 ± 0.22 |
| Gentiobiose | 393.23 ± 0.05 |
| Amygdalin | 377.4 ± 0.21 |
| Cellobiose | 209.18 ± 0.18 |
| Genistin | 175.3 ± 0.3 |
| Glycitin | 75.63 ± 0.6 |

Example 5 Synergetic Degradation of Filter Paper

The activity of filter paper enzyme can be taken as an index measuring the total activity of cellulase system from microorganism, directly indicating cellulase's hydrolysis capacity.

As assay group, 100 uL of supernatant of specific *humicola* culture and 100 uL of β-glucosidase BGL3A solution diluted with dilution factor of 1, 10 and 50 corresponding to 30 U, 3 U and 0.6 U were added to citric acid-sodium dimetallic phosphate buffer (pH 4.5) using Whatman quantitative filter paper as substrate, to react for 1 h at 50° C., and the amount of reducing sugars was measured by DNS method. As a control, 100 uL of buffer substituting enzyme was added. The result showed assay groups had 1.296 times, 1.198 times and 1.129 times higher filter paper enzyme activity relative to the supernatant of specific *humicola* culture. As a result, β-glucosidase BGL3A had good capability of hydrolyzing cellulose, and synergistically decomposing complex substrates with exo-cellulase and cellobiohydrolase.

The invention claimed is:

1. A recombinant host cell comprising a heterologous acid β-glucosidase comprising the amino acid sequence of SEQ ID NO: 1 or SEQ ID NO: 2.

2. An isolated polynucleotide encoding the acid-β-glucosidase comprised in the recombinant host cell of claim 1.

3. A DNA constructor or a recombinant vector comprising the isolated polynucleotide of claim 2.

4. A recombinant vector pPIC9-bgl3A comprising the polynucleotide of claim 2.

5. A recombinant host cell comprising the isolated polynucleotide of claim 2.

6. A recombinant host cell GS115/bgl3 comprising the isolated polynucleotide of claim 2.

7. A method of producing a high-temperature acid β-glucosidase comprising the steps of:
  (1) transforming a host cell with the DNA constructor or a recombinant vector of claim 3 to obtain the recombinant host cell;
  (2) cultivating the recombinant host cell to induce expression of β-glucosidase; and
  (3) recovering said high-temperature acid β-glucosidase.

8. The recombinant host cell of claim 1, said acid β-glucosidase having an optimal pH value of 4.5 and an optimal temperature of 75° C., and being thermostable at 37° C., and maintaining over 90% of activity in an optimal condition after being processed at 60° C. for 1 hour.

9. The recombinant host cell of claim 1, wherein said cell is a yeast cell.

10. The recombinant host cell of claim 9, wherein said yeast cell is a *Pichia* cell.

11. The recombinant host cell of claim 9, wherein said yeast cell is an *Aspergillus* cell.

12. The recombinant host cell of claim 1, wherein said cell is an *E. coli* cell.

* * * * *

SEQUENCE LISTING

<160> NUMBER OF SEQ ID NOS: 14

<210> SEQ ID NO 1
<211> LENGTH: 737
<212> TYPE: PRT
<213> ORGANISM: Talaromyces emersonii 12802

<400> SEQUENCE: 1

```
Met Leu Ala Glu Gln Ile Phe Leu Ser Val Leu Ala Ala Val Thr
 1               5                  10                  15

Val Gln Ala Tyr Gly Phe Gly Gly Ser Gly Trp Asp Ala Ala Tyr Gly
            20                  25                  30

Arg Ala Lys Ala Ala Leu Asn Lys Leu Asn Gln Thr Glu Lys Val Gly
            35                  40                  45

Ile Val Thr Gly Val Lys Trp Met Gly Pro Cys Val Gly Asn Thr
 50                  55                  60

Tyr Lys Pro Ser Ser Ile Asp Tyr Pro Ser Leu Cys Leu Gln Asp Ser
 65                  70                  75                  80

Pro Leu Gly Val Arg Phe Ala Asn Pro Val Thr Ala Phe Pro Ala Gly
            85                  90                  95

Ile Asn Ala Gly Ala Thr Trp Asp Arg Ser Leu Ile Asn Ala Arg Gly
            100                 105                 110

Ala Ala Met Gly Ala Glu Ala Lys Gly Leu Gly Val Asn Val Gln Leu
            115                 120                 125

Gly Pro Val Ala Gly Pro Leu Gly Lys Asn Pro Asn Ser Gly Arg Ile
130                 135                 140

Trp Glu Gly Phe Ser Asn Asp Pro Tyr Leu Ser Gly Val Ala Met Glu
145                 150                 155                 160

Glu Thr Ile Ala Gly Met Gln Gly Ser Gly Val Gln Ala Cys Ala Lys
                165                 170                 175

His Tyr Ile Gly Asn Glu Gln Glu His Asn Arg Glu Thr Ile Ser Ser
                180                 185                 190

Asn Ile Asp Asp Arg Thr Leu His Glu Leu Tyr Val Trp Pro Phe Met
            195                 200                 205

Asn Ala Val Lys Ala Asn Val Ala Ser Val Met Cys Ser Tyr Asn Glu
210                 215                 220

Val Asn Gly Ser Trp Ser Cys Glu Asn Asp Ala Leu Leu Asn Gly Leu
225                 230                 235                 240

Leu Lys Thr Glu Leu Gly Phe Pro Gly Tyr Ile Met Ser Asp Trp Asn
                245                 250                 255

Ala Gln His Thr Thr Val Asn Ser Ala Asn Ser Gly Leu Asp Met Thr
            260                 265                 270

Met Pro Gly Ser Asp Phe Asn Asn Pro Gly Ser Ile Tyr Trp Gly
            275                 280                 285

Pro Asn Leu Glu Ala Ala Val Ala Asn Gly Ser Val Pro Gln Ser Arg
            290                 295                 300

Leu Asp Asp Met Val Thr Arg Ile Leu Ala Ser Trp Tyr Leu Val Gly
305                 310                 315                 320

Gln Asp Glu Gly Tyr Pro Pro Val Ala Phe Ser Ser Trp Asn Gly Gly
                325                 330                 335

Lys Ala Asn Val Asp Val Thr Gly Asp His Lys Ser Val Val Arg Ala
            340                 345                 350

Val Ala Arg Asp Ser Ile Val Leu Leu Lys Asn Asp Asn Asn Ala Leu
            355                 360                 365
```

```
Pro Leu Arg Lys Pro Lys Ser Leu Ala Ile Ile Gly Gln Asp Ala Thr
    370                 375                 380

Val Asn Pro Ala Gly Pro Asn Ala Cys Ser Asp Arg Gly Cys Asp Thr
385                 390                 395                 400

Gly Thr Leu Ala Met Gly Trp Gly Ser Gly Thr Ala Gln Phe Pro Tyr
                405                 410                 415

Ile Val Gly Pro Leu Asp Ala Ile Gln Ser Gln Ala Ala Asp Gly
                420                 425                 430

Thr Asn Ile Thr Thr Ser Thr Thr Asp Asp Thr Thr Ala Ala Ala Ser
                435                 440                 445

Ala Ala Ala Ser Ala Gly Thr Ala Ile Val Phe Ile Asn Ser Asp Ser
    450                 455                 460

Gly Glu Gly Tyr Ile Thr Val Glu Gly Asn Ala Gly Asp Arg Asn Asn
465                 470                 475                 480

Leu Asp Pro Trp His Asn Gly Asn Glu Leu Val Gln Ala Val Ala Ala
                485                 490                 495

Val Asn Lys Asn Val Ile Val Val His Ser Val Gly Pro Val Ile
                500                 505                 510

Leu Glu Ala Ile Leu Ala Gln Pro Asn Val Lys Ala Ile Val Trp Pro
    515                 520                 525

Gly Leu Pro Gly Gln Glu Ser Gly Asn Ala Leu Val Asp Val Leu Tyr
530                 535                 540

Gly Ser Thr Ser Pro Ser Gly Lys Leu Pro Tyr Thr Ile Ala Lys Gln
545                 550                 555                 560

Phe Ser Asp Tyr Gly Thr Thr Trp Thr Thr Ser Leu Val Asp Asp Phe
                565                 570                 575

Thr Glu Gly Leu Phe Ile Asp Tyr Arg His Phe Asp Glu Asn Asn Ile
                580                 585                 590

Thr Pro Arg Tyr Glu Phe Gly Tyr Gly Leu Ser Tyr Thr Thr Phe Lys
    595                 600                 605

Tyr Ser Asp Leu Asp Val Asn Val Gln Ala Arg Pro Gly Ala Ala Glu
610                 615                 620

Gly Pro Ile Val Pro Gly Val Lys Glu Leu Phe Asp Thr Val Gly
625                 630                 635                 640

Thr Val Thr Val Thr Val Gln Asn Ser Gly Lys Val Ala Gly Ala Glu
                645                 650                 655

Val Ala Gln Leu Tyr Ile Gly Leu Pro Asp Ser Ala Pro Ser Thr Pro
                660                 665                 670

Pro Lys Gln Leu Arg Gly Phe Gln Lys Leu His Leu Ala Pro Gly Gln
    675                 680                 685

Arg Glu Gly Ala Thr Phe Glu Leu Thr Arg Arg Asp Ile Ser Tyr Trp
690                 695                 700

Asp Val Gln Gln Gln Lys Trp Val Val Pro Ser Gly Thr Phe Lys Val
705                 710                 715                 720

Tyr Val Gly Ser Ser Ser Arg Asp Ile Arg Glu Gln Gly Ser Phe Arg
                725                 730                 735

Ile

<210> SEQ ID NO 2
<211> LENGTH: 718
<212> TYPE: PRT
<213> ORGANISM: Talaromyces emersonii 12802
```

```
<400> SEQUENCE: 2

Tyr Gly Phe Gly Gly Ser Gly Trp Asp Ala Ala Tyr Gly Arg Ala Lys
1               5                   10                  15

Ala Ala Leu Asn Lys Leu Asn Gln Thr Glu Lys Val Gly Ile Val Thr
            20                  25                  30

Gly Val Lys Trp Met Gly Gly Pro Cys Val Gly Asn Thr Tyr Lys Pro
        35                  40                  45

Ser Ser Ile Asp Tyr Pro Ser Leu Cys Leu Gln Asp Ser Pro Leu Gly
    50                  55                  60

Val Arg Phe Ala Asn Pro Val Thr Ala Phe Pro Ala Gly Ile Asn Ala
65                  70                  75                  80

Gly Ala Thr Trp Asp Arg Ser Leu Ile Asn Ala Arg Gly Ala Ala Met
                85                  90                  95

Gly Ala Glu Ala Lys Gly Leu Gly Val Asn Val Gln Leu Gly Pro Val
            100                 105                 110

Ala Gly Pro Leu Gly Lys Asn Pro Asn Ser Gly Arg Ile Trp Glu Gly
        115                 120                 125

Phe Ser Asn Asp Pro Tyr Leu Ser Gly Val Ala Met Glu Glu Thr Ile
130                 135                 140

Ala Gly Met Gln Gly Ser Gly Val Gln Ala Cys Ala Lys His Tyr Ile
145                 150                 155                 160

Gly Asn Glu Gln Glu His Asn Arg Glu Thr Ile Ser Ser Asn Ile Asp
                165                 170                 175

Asp Arg Thr Leu His Glu Leu Tyr Val Trp Pro Phe Met Asn Ala Val
            180                 185                 190

Lys Ala Asn Val Ala Ser Val Met Cys Ser Tyr Asn Glu Val Asn Gly
        195                 200                 205

Ser Trp Ser Cys Glu Asn Asp Ala Leu Leu Asn Gly Leu Leu Lys Thr
    210                 215                 220

Glu Leu Gly Phe Pro Gly Tyr Ile Met Ser Asp Trp Asn Ala Gln His
225                 230                 235                 240

Thr Thr Val Asn Ser Ala Asn Ser Gly Leu Asp Met Thr Met Pro Gly
                245                 250                 255

Ser Asp Phe Asn Asn Pro Pro Gly Ser Ile Tyr Trp Gly Pro Asn Leu
            260                 265                 270

Glu Ala Ala Val Ala Asn Gly Ser Val Pro Gln Ser Arg Leu Asp Asp
        275                 280                 285

Met Val Thr Arg Ile Leu Ala Ser Trp Tyr Leu Val Gly Gln Asp Glu
290                 295                 300

Gly Tyr Pro Pro Val Ala Phe Ser Ser Trp Asn Gly Gly Lys Ala Asn
305                 310                 315                 320

Val Asp Val Thr Gly Asp His Lys Ser Val Val Arg Ala Val Ala Arg
                325                 330                 335

Asp Ser Ile Val Leu Leu Lys Asn Asp Asn Asn Ala Leu Pro Leu Arg
            340                 345                 350

Lys Pro Lys Ser Leu Ala Ile Ile Gly Gln Asp Ala Thr Val Asn Pro
        355                 360                 365

Ala Gly Pro Asn Ala Cys Ser Asp Arg Gly Cys Asp Thr Gly Thr Leu
370                 375                 380

Ala Met Gly Trp Gly Ser Gly Thr Ala Gln Phe Pro Tyr Ile Val Gly
385                 390                 395                 400

Pro Leu Asp Ala Ile Gln Ser Gln Ala Ala Ala Asp Gly Thr Asn Ile
            405                 410                 415
```

```
Thr Thr Ser Thr Thr Asp Asp Thr Thr Ala Ala Ser Ala Ala Ala
            420                 425                 430

Ser Ala Gly Thr Ala Ile Val Phe Ile Asn Ser Asp Ser Gly Glu Gly
            435                 440                 445

Tyr Ile Thr Val Glu Gly Asn Ala Gly Asp Arg Asn Asn Leu Asp Pro
        450                 455                 460

Trp His Asn Gly Asn Glu Leu Val Gln Ala Val Ala Val Asn Lys
465                 470                 475                 480

Asn Val Ile Val Val His Ser Val Gly Pro Val Ile Leu Glu Ala
                485                 490                 495

Ile Leu Ala Gln Pro Asn Val Lys Ala Ile Val Trp Pro Gly Leu Pro
            500                 505                 510

Gly Gln Glu Ser Gly Asn Ala Leu Val Asp Val Leu Tyr Gly Ser Thr
            515                 520                 525

Ser Pro Ser Gly Lys Leu Pro Tyr Thr Ile Ala Lys Gln Phe Ser Asp
            530                 535                 540

Tyr Gly Thr Thr Trp Thr Thr Ser Leu Val Asp Asp Phe Thr Glu Gly
545                 550                 555                 560

Leu Phe Ile Asp Tyr Arg His Phe Asp Glu Asn Asn Ile Thr Pro Arg
                565                 570                 575

Tyr Glu Phe Gly Tyr Gly Leu Ser Tyr Thr Thr Phe Lys Tyr Ser Asp
            580                 585                 590

Leu Asp Val Asn Val Gln Ala Arg Pro Gly Ala Ala Glu Gly Pro Ile
                595                 600                 605

Val Pro Gly Gly Val Lys Glu Leu Phe Asp Thr Val Gly Thr Val Thr
610                 615                 620

Val Thr Val Gln Asn Ser Gly Lys Val Ala Gly Ala Glu Val Ala Gln
625                 630                 635                 640

Leu Tyr Ile Gly Leu Pro Asp Ser Ala Pro Ser Thr Pro Pro Lys Gln
                645                 650                 655

Leu Arg Gly Phe Gln Lys Leu His Leu Ala Pro Gly Gln Arg Glu Gly
            660                 665                 670

Ala Thr Phe Glu Leu Thr Arg Arg Asp Ile Ser Tyr Trp Asp Val Gln
            675                 680                 685

Gln Gln Lys Trp Val Val Pro Ser Gly Thr Phe Lys Val Tyr Val Gly
        690                 695                 700

Ser Ser Ser Arg Asp Ile Arg Glu Gln Gly Ser Phe Arg Ile
705                 710                 715

<210> SEQ ID NO 3
<211> LENGTH: 19
<212> TYPE: PRT
<213> ORGANISM: Talaromyces emersonii 12802

<400> SEQUENCE: 3

Met Leu Ala Glu Gln Ile Phe Leu Ser Val Leu Ala Ala Ala Val Thr
1               5                   10                  15

Val Gln Ala

<210> SEQ ID NO 4
<211> LENGTH: 2682
<212> TYPE: DNA
<213> ORGANISM: Talaromyces emersonii 12802
<220> FEATURE:
<221> NAME/KEY: misc_feature
<222> LOCATION: (119)..(119)
<223> OTHER INFORMATION: n is a, c, g, or t
```

```
<220> FEATURE:
<221> NAME/KEY: misc_feature
<222> LOCATION: (134)..(134)
<223> OTHER INFORMATION: n is a, c, g, or t
<220> FEATURE:
<221> NAME/KEY: misc_feature
<222> LOCATION: (292)..(292)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (455)..(455)
<223> OTHER INFORMATION: n is a, c, g, or t

<400> SEQUENCE: 4
agcgccgcac tccagtattc cggtgatttc cagcgacatt gatgcgggga aggaatcaag      60
gggacatcat ccctggaatt cctataagat ggccgtcacc cacgcatgaa aaataaaana     120
tgctcctttt gatntgcgac tcgagtaccc acagcgacag cgacgatcac catgcttgct     180
gagcaaatct tcctgagtgt tctggcagca gccgtcactg tccaggccta tggcttcggc     240
ggctctggct gggacgccgc ttatggcaga gcaaaggctg cgctgaacaa gntcaaccag     300
accgagaagg ttggtatcgt caccggtgtc aagtggatgg gcggcccttg tgttggcaac     360
acctacaagc ccagttcgat tgantaccct tctctgtgtt tgcaagactc tcctctcggg     420
gtgcgttttg ccaaccctgt gactgccttc ccggntggta tcaacgccgg cgccacatgg     480
gatagatctc tcatcaacgc ccgtggtgcg gccatgggcg ctgaggccaa gggcctcggt     540
gtgaacgtcc agcttggccc cgtcgctggt cctctcggca agaatcccaa tagtggcaga     600
atctgggaag ggttctcgaa tgatccctat ctcagcggtg ttgcgatgga ggaaaccatc     660
gccggaatgc aaggatctgg tgtgcaggcc tgcgccaagg tacgtggatc tcgttcttgc     720
aacatgtacg atctgttgag ggctgacacg atacctgaat ctatagcact atattggtaa     780
cgagcaagag cacaaccgtg aaaccatcag ctccaacatc gatgaccgca ctctgcacga     840
gctctacgtc tggccgttca tgaacgccgt caaggccaac gtcgcctccg tcatgtgctc     900
gtacaacaag gtcaatggtt cctggtcctg tgagaatgat gctcttctca acggtctgtt     960
gaagactgag ctcggattcc ccggatacat catgagcgat tggaacgcgc agcacaccac    1020
ggtcaacagc gccaactcgg gtctcgatat gaccatgcct ggcagtgact caacaacccc    1080
tcctggcagc atctgctggg ggcccaacct cgaagccgcc gtcgccaatg gctccgttcc    1140
gcagtcccgt ttggacgaca tggtcactcg tatccttgcg tcttggcact tggttggcca    1200
ggatgagggc tacccaccgg tcgccttcag ctcctggaat ggcggcaagg ccaatgttga    1260
cgtgacgggc gatcacaaga gcgtcgtcag agctgtggct cgtgactcta ccgttcttct    1320
gaagaacgac aataacgctt tgcctctgcg caagcccaag agcctcgcga tcatcggcca    1380
ggatgcaacc gtcaaccctg ccgggcccaa cgcttgctct gatcgcggct gcgacactgg    1440
tactctcgcc atgggttggg gcagtggtac cgctcagttc ccagtgagtc gtcccattgc    1500
aacttccaca ggagcgaccg gtgactaaca agcacctagt acatcgtcgg ccctctcgat    1560
gctatccagt ctcaggctgc cgctgatggc actaacatca ccaccagcgc gaccgatgat    1620
accaccgcgg cagcttctgc agccgcctcc gccggaaccg ccatcgtctt catcaactcc    1680
gactctggtg aagggtaagc ccgggcgtca agatcctcgt acagatgggc ccgcatcgct    1740
aacattctac agttacatca ccgtcgaggg caacgctggt gaccgcaaca acctcgaccc    1800
```

```
ctggcacaac ggcaacgagc tcgtccaggc cgttgcggct gcgaacaaga atgtcattgt    1860
cgtcgtccac agcgtcggtc ccgtgatctt ggagactatc cttgcacagc ccaacgtcaa    1920
ggccattgtg tggcccggtc tccctggaca agagagcggc aatgccctgg tcgatgttct    1980
gtacggctcc acctccccca gcggcaagtt gccctatacc attgccaagc agttcagcga    2040
ctatggctcc acctggacga cctccctggt cgatgacttc accgagggtc tgttcattga    2100
ctaccgccac tttgacgaga acaacattac tcccagatac gagttcggat acggcttgtg    2160
ttagtacttc cttctctctc tcgtagatcc atgctgtctt tgcaacgaca caaactgaca    2220
tgataatagc ttacaccacc ttcaaatact ccgacctgga cgtcaacgtc caggcccgcc    2280
ccggcgcagc cgaaggcccc atcgtccccg gcggcgtcaa ggaacttttc gacaccgtcg    2340
gcaccgtcac cgtcaccgtc cagaacagcg gcaaggttgc cggcgcggaa gttgcccagc    2400
tgtacatcgg ccttcccgac tctgccccgt cgacccctcc caagcagctc agaggattcc    2460
agaagttgca cctcgcgccc ggccagagag agggcgccac tttcgaactc acccgccgag    2520
acatcagcta ctgggacgtt cagcagcaga agtgggttgt tcctagcggt acgttcaagg    2580
tctatgttgg aagctcgagc agggacatta gggagcaggg atcttgttgt acgagcacat    2640
gacggaggcg acgttgaccg tggtgtgctg cgcgttccaa tc                      2682

<210> SEQ ID NO 5
<211> LENGTH: 2157
<212> TYPE: DNA
<213> ORGANISM: Talaromyces emersonii 12802

<400> SEQUENCE: 5
tatggcttcg gcggctctgg ctgggacgcc gcttatggca gagcaaaggc tgcgctgaac      60
aagctcaacc agaccgagaa ggttggtatc gtcaccggtg tcaagtggat gggcggccct     120
tgtgttggca acacctacaa gcccagttcg attgactacc cttctctgtg tttgcaagac     180
tctcctctcg gggtgcgttt tgccaaccct gtgactgcct tcccggctgg tatcaacgcc     240
ggcgccacat gggatagatc tctcatcaac gcccgtggtg cggccatggg cgctgaggcc     300
aagggcctcg gtgtgaacgt ccagcttggc cccgtcgctg gtcctctcgg caagaatccc     360
aatagtggca gaatctggga agggttctcg aatgatccct atctcagcgg tgttgcgatg     420
gaggaaacca tcgccggaat gcaaggatct ggtgtgcagg cctgcgccaa gcactatatt     480
ggtaacgagc aagagcacaa ccgtgaaacc atcagctcca acatcgatga ccgcactctg     540
cacgagctct acgtctggcc gttcatgaac gccgtcaagg ccaacgtcgc ctccgtcatg     600
tgctcgtaca acgaggtcaa tggttcctgg tcctgtgaga atgatgctct tctcaacggt     660
ctgttgaaga ctgagctcgg attccccgga tacatcatga gcgattggaa cgcgcagcac     720
accacggtca acagcgccaa ctcgggtctc gatatgacca tgcctggcag tgacttcaac     780
aaccctcctg gcagcatcta ctgggggccc aacctgaaag ccgccgtcgc caatggctcc     840
gttccgcagt cccgtttgga cgacatggtc actcgtatcc ttgcgtcttg gtacttggtt     900
ggccaggatg agggctaccc accggtcgcc ttcagctcct ggaatggcgg caaggccaat     960
gttgacgtga cggcgatca caagagcgtc gtcagagctg tggctcgtga ctctatcgtt    1020
cttctgaaga acgacaataa cgctttgcct ctgcgcaagc ccaagagcct cgcgatcatc    1080
ggccaggatg caactgtcaa ccctgccggg cccaacgctt gctctgatcg cggctgcgac    1140
accggtactc tcgccatggg ttggggcagt ggtaccgctc agttcccata catcgtcggc    1200
cctctcgatg ctatccagtc tcaggctgcc gctgatggca ctaacatcac caccagcacg    1260
```

-continued

```
accgatgata ccaccgcggc agcttctgca gccgcctccg ccggaaccgc catcgtcttc  1320
atcaactccg actctggtga aggttacatc accgtcgagg gcaacgctgg tgaccgcaac  1380
aacctcgacc cctggcacaa cggcaacgag ctcgtccagg ccgttgcggc tgtgaacaag  1440
aatgtcattg tcgttgtcca cagcgtcggt cccgtgatct tggaggctat ccttgcacag  1500
cccaacgtca aggccattgt gtggcccggt ctccctggac aagagagcgg caatgccctg  1560
gtcgatgttc tgtacggctc cacctccccc agcggcaagt tgccctatac cattgccaag  1620
cagttcagcg actatggcac cacctggacg acctccctgg tcgatgactt caccgagggt  1680
ctgttcattg actaccgcca ctttgacgag aacaacatta ctcccagata cgagttcgga  1740
tacggcttgt cttacaccac cttcaaatac tccgacctgg acgtcaacgt ccaggcccgc  1800
cccggcgcag ccgaaggccc catcgtcccc ggcggcgtca aggaacttt cgacaccgtc  1860 ggcaccgtca ccgtcaccgt ccagaacagc ggcaaggttg ccggcgcgga agttgcccag  1920
ctgtacatcg gccttcccga ctctgccccg tcgaccccctc ccaagcagct cagaggattc  1980
cagaagttgc acctcgcgcc cggccagaga gagggcgcca ctttcgaact cacccgccga  2040
gacatcagct actgggacgt tcagcagcag aagtgggttg ttcctagcgg tacgttcaag  2100
gtctatgttg gaagctcgag cagggacatt agggagcagg atctttccg tatttga    2157
```

<210> SEQ ID NO 6
<211> LENGTH: 57
<212> TYPE: DNA
<213> ORGANISM: Talaromyces emersonii 12802

<400> SEQUENCE: 6

```
atgcttgctg agcaaatctt cctgagtgtt ctggcagcag ccgtcactgt ccaggcc       57
```

<210> SEQ ID NO 7
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (18)..(18)
<223> OTHER INFORMATION: n is a, c, g, or t

<400> SEQUENCE: 7

```
ggccgcaayt gggarggntt                                                20
```

<210> SEQ ID NO 8
<211> LENGTH: 21
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (13)..(13)
<223> OTHER INFORMATION: n is a, c, g, or t

<400> SEQUENCE: 8

```
gtcaccaggc atnghcatrt c                                              21
```

<210> SEQ ID NO 9
<211> LENGTH: 25
<212> TYPE: DNA
<213> ORGANISM: Artificial Sequence
<220> FEATURE:
<223> OTHER INFORMATION: primer -continued

```
<400> SEQUENCE: 9
cgaggacgga acctaccgcg agagc                                              25

<210> SEQ ID NO 10
<211> LENGTH: 26
<212> TYPE: DNA
<213> ORGANISM: Artificial Sequence
<220> FEATURE:
<223> OTHER INFORMATION: primer

<400> SEQUENCE: 10
cgaggagtac atcaagcttg ccttcg                                             26

<210> SEQ ID NO 11
<211> LENGTH: 23
<212> TYPE: DNA
<213> ORGANISM: Artificial Sequence
<220> FEATURE:
<223> OTHER INFORMATION: primer

<400> SEQUENCE: 11
caaggtcgac cctaaggcca agc                                                23

<210> SEQ ID NO 12
<211> LENGTH: 24
<212> TYPE: DNA
<213> ORGANISM: Artificial Sequence
<220> FEATURE:
<223> OTHER INFORMATION: primer

<400> SEQUENCE: 12
gtagagcttg gccttagggt cgac                                               24

<210> SEQ ID NO 13
<211> LENGTH: 24
<212> TYPE: DNA
<213> ORGANISM: Artificial Sequence
<220> FEATURE:
<223> OTHER INFORMATION: primer

<400> SEQUENCE: 13
gcggcggtct cgaaggcaag cttg                                               24

<210> SEQ ID NO 14
<211> LENGTH: 24
<212> TYPE: DNA
<213> ORGANISM: Artificial Sequence
<220> FEATURE:
<223> OTHER INFORMATION: primer

<400> SEQUENCE: 14
ggtaggttcc gtcctcgttc agcg                                               24
```